(12) United States Patent
Castex-Rizzi et al.

(10) Patent No.: US 11,484,555 B2
(45) Date of Patent: Nov. 1, 2022

(54) BACTERIAL SECRETOME FOR USE IN THE TREATMENT OF SKIN LESIONS

(71) Applicant: PIERRE FABRE DERMO-COSMETIQUE, Boulogne-Billancourt (FR)

(72) Inventors: Nathalie Castex-Rizzi, Colomiers (FR); Marie Florence Galliano, Blagnac (FR); Hélène Hernandez-Pigeon, Cugnaux (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 271 days.

(21) Appl. No.: 16/603,002

(22) PCT Filed: Apr. 6, 2018

(86) PCT No.: PCT/EP2018/058929
§ 371 (c)(1),
(2) Date: Oct. 4, 2019

(87) PCT Pub. No.: WO2018/185324
PCT Pub. Date: Oct. 11, 2018

(65) Prior Publication Data
US 2020/0030387 A1 Jan. 30, 2020

(30) Foreign Application Priority Data
Apr. 6, 2017 (FR) .................................... 1753012

(51) Int. Cl.
| | | |
|---|---|---|
| *A61K 35/74* | (2015.01) | |
| *A61K 8/99* | (2017.01) | |
| *A61K 33/30* | (2006.01) | |
| *A61K 33/34* | (2006.01) | |
| *A61Q 19/08* | (2006.01) | |
| *C12N 1/20* | (2006.01) | |
| *C12R 1/36* | (2006.01) | |

(52) U.S. Cl.
CPC ............... *A61K 35/74* (2013.01); *A61K 8/99* (2013.01); *A61K 33/30* (2013.01); *A61K 33/34* (2013.01); *A61Q 19/08* (2013.01); *C12N 1/20* (2013.01); *C12N 1/205* (2021.05); *C12R 2001/36* (2021.05)

(58) Field of Classification Search
None
See application file for complete search history.

(56) References Cited

U.S. PATENT DOCUMENTS 9,662,357 B2 * 5/2017 Lebaron ............... A61Q 19/007

FOREIGN PATENT DOCUMENTS

| EP | 1787651 A1 | 5/2007 |
|---|---|---|
| WO | WO 2012/085182 A1 | 6/2012 |
| WO | WO 2012/085183 A1 | 6/2012 |
| WO | WO 2014/045280 A1 | 3/2014 |

OTHER PUBLICATIONS

French Search Report for French Application No. 1753012, completed Nov. 20, 2017.
Guèniche et al., "Improvement of atopic dermatitis skin symptoms by Vitreoscila filiformis bacterial extract," Eur J Dermatol, vol. 16, No. 4, Jul.-Aug. 2006, pp. 380-384.
International Search Report for International Application No. PCT/EP2018/058929, dated May 14, 2018.
Needleman et al., "A General Method Applicable to the Search for Similarities in the Amino Acid Sequence of Two Proteins," J. Mol. Biol., vol. 48, 1970, pp. 443-453.
Pearson et al., "Improved tools for biological sequence comparison," Proc. Nat. Acad. Sci. USA, vol. 85, Apr. 1988, pp. 2444-2448.
Pollok et al., "Connexin 43 mimetic peptide Gap27 reveals potential differences in the role of Cx43 in wound repair between diabetic and non-diabetic cells," J. Cell. Mol. Med., vol. 15, No. 4, 2011, pp. 861-873.
Smith et al., "Comparison of Biosequences," Advances in Applied Mathematics, vol. 2, 1981, pp. 482-489.
Tatusova et al., "BLAST 2 Sequences, a new tool for comparing protein and nucleotide sequences." FEMS Microbiology Letters, vol. 174, 1999, pp. 247-250.
Witte et al., "General Principles of Wound Healing," Wound Healing, vol. 77, No. 3, Jun. 1997, pp. 509-528.

* cited by examiner

*Primary Examiner* — Oluwatosin A Ogunbiyi
(74) *Attorney, Agent, or Firm* — Birch, Stewart, Kolasch & Birch, LLP (57) ABSTRACT

The present invention relates to a novel use of a bacterial secretome in the field of the treatment of skin lesions and more particularly of wound healing. The invention also relates to cosmetic or dermatological compositions comprising such a bacterial secretome as active agent.

13 Claims, 4 Drawing Sheets
Specification includes a Sequence Listing.

SEQUENCE LISTING

<160> NUMBER OF SEQ ID NOS: 2

<210> SEQ ID NO 1
<211> LENGTH: 1487
<212> TYPE: DNA
<213> ORGANISM: artificial
<220> FEATURE:
<223> OTHER INFORMATION: Nouvelle bactirie LMB64, classe des beta-
      proteobacteria, issue d'une nappe phriatique

<400> SEQUENCE: 1
agtttgatca tggctcagat tgaacgcggg cggcatgctt tacacatgca agtcgaacgg      60
cagcacgggc ttcggcctgg tggcgagtgg cgaacgggtg agtaatgcgt cggaacgcgc     120
cgagtagtgg gggataacgc agcgaaagct gtgctaatac cgcatacgta ctgaggtaga     180
aagtggggga ccttcgggcc tcacgctatt cgagcggccg acgtctgatt agctagttgg     240
tggggtaaag gcccaccaag gcgacgatca gtagcgggtc tgagaggatg atccgccaca     300
ctgggactga gacacggccc agactcctac gggaggcagc agtggggaat tttggacaat     360

```
gggcgcaagc ctgatccagc catgccgcgt gtctgaagaa ggccttcggg ttgtaaagga      420
cttttgtccg ggagcaaagc ctgcttgtta ataccgagtg gggatgagag taccggaaga      480
ataagcaccg gctaactacg tgccagcagc cgcggtaata cgtagggtgc aagcgttaat      540
cggaattact gggcgtaaag cgtgcgcagg cggttgtgca agtctgatgt gaaagccccg      600
ggctcaacct gggaacggca ttggagactg cacggctaga gtgcgtcaga gggggtaga      660
attccacgtg tagcagtgaa atgcgtagag atgtggagga ataccgatgg cgaaggcagc      720
cccctgggat gacactgacg ctcatgcacg aaagcgtggg gagcaaacag gattagatac      780
cctggtagtc cacgccctaa acgatgtcaa ttagctgttg ggggtttgaa tccttggtag      840
cgaagctaac gcgtgaaatt gaccgcctgg ggagtacggc cgcaaggtta aaactcaaag      900
gaattgacgg ggacccgcac aagcggtgga tgatgtggat taattcgatg caacgcgaaa      960
aaccttacct gctcttgaca tgtaccgaag cctgaagaga tttgggtgtg cccgaaaggg     1020
agcggtaaca caggtgctgc atggctgtcg tcagctcgtg tcgtgagatg ttgggttaag     1080
tcccgcaacg agcgcaaccc ttgtcattag ttgccatcat ttggttgggc actctaatga     1140
gactgccggt gacaaaccgg aggaaggtgg ggatgacgtc aagtcctcat ggcccttatg     1200
agcagggctt cacacgtcat acaatggtcg gtacagaggg tcgccaagcc gcgaggtgga     1260
gccaatctca gaaagccgat cgtagtccgg atcgcactct gcaactcgag tgcgtgaagt     1320
cggaatcgct agtaatcgca gatcagcatg ctgcggtgaa tacgttcccg ggtcttgtac     1380
acaccgcccg tcacaccatg ggagtggggg ataccagaag tgggtaggct aaccgcaagg     1440
gaggccgctt accacggtat gcttcatgac tggggtgaag tcgtaac                   1487
```

<210> SEQ ID NO 2
<211> LENGTH: 10948
<212> TYPE: DNA
<213> ORGANISM: artificial
<220> FEATURE:
<223> OTHER INFORMATION: Nouvelle bactirie LMB64, classe des beta-
      proteobacteria, issue d'une nappe phriatique

<400> SEQUENCE: 2

```
gggcgcagca ccatcgccca ggccaaaagc cacccgtgcc gattcggcgg cctgttgctc       60
gcgctcaatg cgctgcgcct ggtcggccaa gtcggcggct tgctgctcgg ccttgccccgc     120
cagggtgtca cgctcgcggg tcagttccgc cacctgctcg gctagggcat cgcgctcggc     180
ctcgatcacc tcaccagcgg ccgccagctc ggcggcttcg ctctgcgcct ggaccaagcg     240
gccctcgacc tcggcgcggg cctgggcggc tgcgcgctcg atctcggcgg caatggcggc     300
ggtcaatgcc tggggcagtt ccggcgcagc agcagcggcc accggccggg cctctcgcca     360
ggcagttaga tgcttgtgaa cggtattcgg gctgccggtg cccaaacgct cgcggatcgc     420
gcggatagtc ggctgctgcc cttcgccgac cagcgcatca cgggcggcgg cgaacgggtg     480
gcccgtgcag aggcccgcgt cgagcagatc gagcagcagg ccgccaaggc ggcacaggcc     540
cacgaagaag cccgcgccgc cgccacgcag gaagcccggc aagtgcaagc cgaacgcgac     600
gaagcccgca aggtggccgc cgaggcgcgc gagcagaccg cgcgcctggc tgggcaactc     660
gaagccctca ccgcgaagga gcgaaaagcc gatgaaagac cgtgaccaca acgaagcgat     720
ggccggcatg tttcaggccg accccgatt tgccgccgac tatctgcgcc aggtgttggc      780
cgatggcgag cctaccgacg tgcgcgccgg cttgcgcgcaa atggcggatg tgctgcgcgt     840
cagtcaggcc gccgcgccga ccgattctgc gccttcggcg ggcctctttg accgggccgg     900
```

```
cgtgcgctac gaagtggcgt gcgatgtgat cggggcgttg attgcccatt acgccgaaat    960
catgggacgg gaacgcgagc aggcgcagcc gaatgaggcg gttttgcgcg tggccggagc   1020
catgaaggcg gcgctggccg gggagcggga tgatctcgat ccgcgcgata gcgccggcat   1080
cgaggcggcg atttcgcgct atgcgccact ggcgcgccgg ctgtatggcc aggctgaaaa   1140
cgaccacgcc cgccaggaac agcgtcgcgc cgatttcgac caggtgcatg cttcgctggc   1200
cttggagggg ctggccatga gcgcggacga tttggcggtt caggcgctgc tgatccgggg   1260
cgacattacc cacgatgagg cggtgcagtg ctaccgcatc ctgcatcgcc atgcgcggta   1320
aaaccgactg gccgcccgag gtggccggtg tgctgggttt gctcgaatcg cagccgccag   1380
aggcggcgat gctggtgggc tgttttctgg cggcggtagc ccatcccgat catgcggccg   1440
aattggcgat gttcgacaaa ttgccgccag cggcccggat ggtcgtcggg cgattttttcc   1500 tcgttttttct ggcgggcggc ctggacgatg ccgggcgcga aaaactgcat cgcacatgc   1560 aggcatggtt tgtccgtcag cgccgttttc ggtgaatggc ttgcctcatc cactagggcc   1620
gggcaagggg tgaacagcgg gcgatgctgg cttgcgggac gaccccgcac ccccggaaaa   1680
cttgtcacac accacgcaac tcccgttgct tcgctaaaag ccttgtgccg caaggctttt   1740
agcgaggcga caccgaagac acatcgcggc gacaccgaaa gggccgaacc ggcctaaaac   1800
ccttgctgcg caaggagaac agccgcgctt tcgcgcgcga aagtgcttca aatgcctgtc   1860
ggcatcagca gggtatggat cggcacgccg aaggcgttgg cgatgcgctc caggttgtcc   1920
aaggagatgt ttctgacttg gcgctcgcag tgcgcaacga aggtgcgatg taggccgcac   1980
tcaaaggcga gcgcttcttg tgaccagcct ctttcccggc gtaatcggat catgttggcc   2040
gcgagcacgg cccgcgcgga atgcgcggtt ggtgcgggag gttgagcggc gggagacatg   2100
caaaccagtc tcctgatatg ccgcttttac gtcagccgtg tttaagtcac aatatggttt   2160
tctcatagag aaagacggcg tgacgatggg cagaaaaaca gcaatcaggc gaggggtgc    2220 cgtgttggcc agcctgttga tttgcgcaat tgaaccggtc ggcgcggcct ccctggtcgg   2280
cggtcaaacc gatgattccg tgtgcgacct gggcagcgcg ccacagaacg cccgaagct    2340 gtcggcagcg ggcgacttca tccgcgcgca gtgcaaaaac ggtcaaatgt tggtgggttc   2400
cggcatcgtg cctgccggcg ggtttgactc ggaagtggtg cgcctggcgc gcaccttctg   2460
ccgcatggcg gacattcaga ctcggcgcac gcagggcaac atggccggcc tcgtcatgga   2520
gatcgacgag gtacggtgca tcatcgggaa gttgccgaca tgagaaaagc gatgttggct   2580
ggctttctgg ccgttgtggt ggccaacgtg gttgccgctg agggcggtgc gcccttgcgc   2640
ggcggtgttt gcatcggacc gttccgtggc gctgattccg tcgtgcactg cgagcacatc   2700
ggcaaggtga cgatccgcca gatttacgaa aagggctttc gggtcgttca catgcaggac   2760
gacaagaaca cagccagcta cgttgtgctg gttatcgagg agcaggcgcg atgagggcga   2820
aagcgtggcg gatgctgttt gccggcggc gctgggtgct ctggcttccc gtgccggcgt    2880
cggtatggct ggcactgccc gaatggcagc acattcccgc catgttgttg gcggcctga    2940 tcgtgtggat tcccttctgg ctcgcgtggt ggctcagtga tggcttcgcg ggcatgtcca   3000
ggtggccagg aaccggcgca cctgcggtat ctggcggggt gaacccgcac accggcaagc   3060
catgcacggt gtatcaccag ccgtggggag ataccttcgt gggtggagac tgattatttg   3120
attgaggaac gatgacaagg gccagcaaca agctggccct tgtcgttttc tggactgttt   3180
tacccacaac atccgctctg ctgctgaatt ggcggacatg gcaccgagcc gaacgaacag   3240
```

-continued

```
aacacgcagc aatcccccgg cttggggcgc agcagcgtat ggcaggccgg gcactcgtag    3300
tagaactggc aggcgtccgt gggcatggtt tcctgctgtg cgtggccgca gtgcgggcag    3360
gtcagcacgg attcgagaat gacggcgctc atcgtggcgt tacctctgca cggtggacgg    3420
atagcctgcg ttcgtcgttg ccgaggtcaa cgcttccggc ttggccttgt cggcgtcata    3480
ggtgacggtg gccgttttct tgtcgaaatc gaccttgacg gcgctcacac cgggcacttt    3540
ctccagcgac ttcttgactg tgatcgggca tagctcgcag gtcatgttct gaacggccag    3600
cgtgacggtt ttcggggtgg cggccagcac ggcgagcggc acggcagcca gcagagcaat    3660
cagcagtttg cgcatgggag tctcctttca atagaacagc ggggcgaacc acggcacggc    3720
caacagggca agcaacagca cagtgacgat ccagaacgtc aggcgctgcc gctggcgtgt    3780
gcgcggatca gcgcatggcg tgccgggcgt gcagacctgc ggcaccagat agagcttgcg    3840
gaaggccagt ccgagaaaga gcagcgtcat gccgatgaaa aagggccggt acggctccat    3900
cgcggtcagg ctgccaaccc atgagccacc aatgccaagc accagcagga caagcggccc    3960
gacacagcac accgacgcgc cgatggcggt cagtacgctc acgatcaacg agcttttttc    4020
agtgagtcgt gccatgtcgc tttccttgta cctgtttgcc caagtgttac tctaaatccc    4080
gtacctaagt acgagtcaa gggggtgtga tgggaacaga actgaccatc ggcaagctgg    4140
ctgacgctgc cggggtgaat atcgagacga ttcgctacta ccagcggcgc ggcctgctgg    4200
atgagccgcc taaccgcca gggggcatc ggcgctatgc cctgagcag gcaaaacgtg    4260 tgcgatttat caagcgggca caggcgcttg gtttcacgct ggacgaggta ggcgcgctac    4320
tgaccctgga tgcggcctgc gcctgcgtg agacgcgagc gctggctgtg cgcaagctgg    4380
gtctgatcga gcagaagatg gctgacctcg cggccatgcg gcaggcgctg ggtggattgg    4440
tgcagcagtg tgatgcgggc gacggtggag ccagctgtcc catcatcgac gtgctggcag    4500
gtaattagat gtgttcaaaa aatggtggtt ttctggacac atgccggttt gccctgtcct    4560
gagttgtcct gatgcgttaa agtgttcatt tattcgttca gctttcaatg tggcggaact    4620
gttcatgaat caacgcatcg gctatgcccg cgtttcgacc gacgaccaaa acctagacct    4680
gcaacgggac gcactccggc aggctggatg ctcaaccatt tacgaggaag cagccagcgg    4740
aaagagcgca gcaaggcccg agcttgagca gtgtcggaag gctctccggc ccggcgacac    4800
gcttgtggtg tggcggcttg atcgccttgg gcgcagcctg cccgacctgg tgcagatcgt    4860
ggctgatctt gaacagcgcg gcgtgcattt cgagagcctg accgagaaga tcgagacggg    4920
gagcgcagcg ggtaagctgc aattccatgt tttcgctgca ctcgccgagt tcgagcgcgg    4980
cctgatccgg gagcgaaccc gggcagggct ggatgcagct cgcgcccgtg gccgatccgg    5040
tggacgcaaa ccgaagctgg acgccaagca gatacgccac attaaggcgc tactacgtga    5100
cccgaatacc tgtgttgctg aactcgcccg tgactacggc gtgtcgagaa caactatcta    5160
taaacactgc ggtgtggttc tgccgcgtac agccgatgaa ggggcaatat gacaaaaaag    5220
acaacagcat tcgatgtatt cgagaaatgc gtccaagcag ttcaggctgg tgaactgatc    5280
gaatccgttt ctgcgaagga caaggaattc catttccaga actggtttca gaagcgcctc    5340
cagagcctgt cgatgcactt cgaggggtcg gtcgcaaca cctacccgga cttctgcttg    5400
gtagagcaca ccgagggcta cgagatcaag ggtttggcat ggcctggccg cgagcgcgac    5460
tacgactcga acagccaagt gccgactggc tatcacaacg gccgtcaaat cttctacgtg    5520
ttcgggcgct accccgcaga cctgtctggc tatgccgatc agggcaacgg ccgcaggcag    5580
tacccggtgg ttgacctcgt ggtctgccac ggcgacttcc tcaacgccga tcacaactac    5640
```

-continued

```
gtccataaga acaagagcgt aaagggcttt ggcacctacg gcgacatcat gatccgcgac      5700
cggaagatgt acgtcgcgcc gacgccattt gcgctgaccg aaggcaccac tggcctgatg      5760
actttgatcc tgccggagaa cttcggcacc gatgaccgtt accaggtggt cggtaacctc      5820
actcgcgtcg aggcggaaac gctggtggtt ggctacaact tgacctgcg cacgaacgag       5880 ctgagcgcag agcgcgtgcc caatcccaac gcaggcaccc agcaccgatt cgtggcctac      5940
cggctcaagg atcaagcgag caagcctgtc tccatgactg gcacccaggt gcagcccgac      6000
gagaacaacc tgccggacga cgaatgaaca ccatcaccga caagatcggg ttcgcttacc      6060
cggttgcagc gaccgcgctg gagtgcgact ccccgctggt cgaaatcagc cagatcgccg      6120
agcaggaaag ttggcgaaag gagatcaaca ggccgatcta ccacatccac aagtggtggg      6180
cgaccagact tgggtcggtg tttcgtggca ttacccttgg tgctttgagt cagcctggta      6240
ctgacctctg ggcgcagttc tacaaaacgc acgacctggc cggtaaggta gtgctcgatc      6300
ccttcatggg cagtggcacg acgcttggcg aggccgtcaa gctgggtgcc aaggccatcg      6360
gctgcgacat caacccagtc agtaccttcc tcgtacgtca ggcgttcacg ccggcgtccg      6420
aggcagagct gcgtgccgct ttcgagcggc tggaacgtga cgtggcaccg agattcggc       6480 gctactacca gacgcgcgat cctaagacgg gcgagctgat tcaggtcttg tactacttct      6540
gggtcaagac ggtgacgacg cccgagggcg aggtaatccc cttgctgtcg cgctacgtgt      6600
tttcacaaga cgcctacccg aagaagaagc gcgagcgca gatcgtgtgc cctggctgct       6660
ggagtgtgct ggaggatcgc tacgatgcga ctgacctgca ctgccagcac tgcggccacc      6720
agttcaatcc gcaggaaggc ccggccgctg gtcagtacgt caaaaccaag ggcggtcacc      6780
gttaccgcat caaggaacta ctgccaaagg acggtacgcc gccctctcat cgaatgtacg      6840
cgatgatggc cttgcgagcg gatggatcga aggtctatct gccggtgcgg aatgaggact      6900
tggccctcta cgaggaagcc caagaacgcc ttgctacaga ggcactgccg ctgccgaaaa      6960
cctctgttcg acctggccac aacaccgacc aggcgcgcgg ctacaactac acccaatggc      7020
gcgacttctt caatgcgcgc caactgctgt gccttggcct gctgctgcgg gaaatcctga      7080
ccatcgacga cctggcagtg caagagcaga tgctgtgctt gttctccagc accttggagt      7140
tcaacaacct gttttgcagc ttcaagggtg agggaacagg ggccgtgcgg catatgttct      7200
cgaaccacat cctcaagcca gagcgcaccc cgctggagaa ctccgtgtgg ggcactggca      7260
agagcagcgg tacgtttagc acgttgttcg agtctcgcct gctacgtgcg aagcgctacc      7320
tcgatgagcc gttcgagatc gcgttcgagc atgaccagga cggtaaccgc gcaggctcgc      7380
gcaagacggt ggctagccat ccgatccgcg cccgtcgcgt cgaaacctgg ccggaattgg      7440
aggccgcaga tcatggcctg ctgatcctca acggtgacag ctcgaagctg ccggtgcccg      7500
ctggttcggt ggatgccgtg gtgactgatc cgcccctactt cgacttcgtt cattactcgg     7560
agttgagcga cttcttttttt gcttggctca ccctgtgct gcgccagcgc tatccgtgga      7620
tggcccgcga ggactcgtct gaccaagggg aggtgcagca caaagaccct cgtgtgttcg      7680
cccgtcagct tgcgtcggtg ttcacggagg cgtgccgcgt gcttaaggac gatgagtgt      7740 tggcgttcag cttccaccac tcgcgtgccg agggctgggg ggccatctat gaagcgatca      7800
acaaggcggg cctggccgta gttgcggctc accctgtcca tgccgagctg cgcgcggcaa      7860
gtcccaagac tgcggccaaa gacccgatca gccttgatgc gattctggtg tgtcgcaaaa      7920
aggcgtttgc cctgcaccag tcgcctgcta tccaggatgt ccgccaggct gttgatgcgc      7980
```

```
tggcatcacg gctgcaagct gctggccttc gcatctcggc gggtgaccgc ttcgtgatcg    8040
gcgcagcgca aaccttgatt gcacgcgctg ctgatgacat gggcttcgac gagatcaagg    8100
ttgatcttga ggcaattcgg ctggccgtgg ggccaagggc tgcaacatca aaggctgcga    8160
gtgcgtggga tgacgatgtg cccttctgat tggctgcacg gccttgtcgg cgcatgcgtt    8220
ttgatggcag ccgctgcacg caagccgcgt ccctccgcgt aaagttcatt tatacgcaaa    8280
tacgtatttg cgtgatacaa taacgccata ttaatggagg tgcgtaaatg cggactattg    8340
ttgtggctag ccaaaaaggt ggcgtcggca agacaacgat tgcaggtcac ttgggtgtca    8400 tggcccgagca gagcaaagag gggccagtgg cgctgatcga cacagaccca caaggctcgc    8460
tcgcgtcctg gtggaatgag cgaaccaatg aggcaccgct gtttgcacgg gtggaaatcg    8520
gcaagctgac cgagcacctt caggcattgt ccaagggtgg catcaagctg ccatcatcg     8580 acaccccgcc ctctgttacg gaaatgattc agcaggtgct ccgcaccgcc gacttggtac    8640
tgatccccac caggccgagt ccgcatgact tgcgcgcgt cggatctacc gtcgaactgg     8700
tggagaacgc aggcaagcga atgatcttcg tcatcaatgg ggcggcacct cgcgcgcgga    8760
tcgcgggtga ggctgccgtg gcgctttcgc agcatggcac ggttgccccc gtgacgctgt    8820
accagcgcac cgacttcgcc agctcgatga tcgacgccg caccgtccag gaaatcgacc    8880
ccaaggggcg gtcggccgaa gaaatcgggc agttgtggaa atacgtatct acacaactgc    8940
gtaaaatttg atataatacg tacatgcgta ttaatggaga tacgtaaatg ctaaaactg    9000 catctttgac tgccggcctg gtggccaaga agggggaggc gtccctgct acggttgtcg     9060 cggcacccca ggttcaacct atcgaagtga aggcatcggc gactggcggc ggcccgggatt    9120 actacaaggc gttgaccgtc aagttggatc gtgaccgcta cgagagtctg aaaagcatgg    9180
gcgtgaagct ggacaagaag agccaggaaa tctttgtcga ggccctggat ttgtggatga    9240
agtcggccgc tggccagcaa cacgcctaag aggcccctat gcgttcagtg cgctctgccg    9300
tcgaactcgc caaggagttg gccgaaaaag ccaaggcccg ccgcctagcg gcggaaaaga    9360
acgagctggg acttgaaggc ccggcgcagg gcaacgccgg caccactccc agcccggtga    9420
aggttgcggc cgaagtggtg ggcgagcagc cggcacgacg caagggagcg ccgaaagggc    9480
cgcgtggcct gatgccggtg catcatccaa accgcgattt cttcttgtgc gatctgtttg    9540 actacgcccct aaaggatgac ggcgtgagca tggaggcccc catcttcacc ttggcaacca    9600
ggccggacac ctctgtttgg cattgggaaa gcaaggatgg gacacgcgcc atcaccgtca    9660
cgccaagcgt gaaggggagg gccacgcagt ttgataagga tttacttatt tacgtagtta    9720
gccagatgac cgaggctatc aatcgcggtc ggcctgatgc gaacaatcga accgtgcgct    9780
ttcgcgtcta tgactacttg gtctcaacca caagccgac tggcggcaag gagtaccagc     9840
gactggagga tgccctagac aggctgcggg gtacatcgat caagacgaac atcaagacgg    9900
gtggccagcg tgtgaaggaa ggcttcggca tcgtcgatag ctggacgatc atcgagaagg    9960
cccccgacga tgaccgcatg attgccgtcg aggtcacgct ctccaagtgg cttttcaatg    10020
cagtgcaggc ccacgaggtt ctgaccatca acccggacta tttccggctg cgtaagccaa    10080
ttgagcgccg tttgtacgag ctggccagga agcactgtgg cgaccaggcc ttttttgtga    10140
ttgggctgga actgttgcag gacaagtgcg gcagcaagtc ggcactgttc gagttccgcc    10200
gtgccttgcg cgagatcatc aaggccgaca ccttgccaga ctaccgcatg acgcttgatg    10260
acgagaaaga ccaggtgatt ttctacaccc gcgacgaa gaagctagcg gcgtctaccg    10320
ctctggcccg gcgcttccag tgacgcccaa agtattgacg gtcaatactt cgttatttca    10380
```

```
cccatgcggt gttaccgctg cgtgttggac gttcccttga cctagcggcc gaggcagggc    10440
tttcgcgctt tgcattgagc caccaagtgc gtctcgctcc ttcgagcatc aagccctaac    10500
gcgtttcatg tcactttcgc gcacgaaagt cgaggcaaga ggcttgatcg tgtctatcgt    10560
tacatcaccc atgcctgtgg atggacacgt tacatcaccc atgttttctg tggatgggca    10620
cgttacatca cccatacctc acttcgttac atcgcccatg cagcgatttg tggaagcctt    10680
gagcagcaag gctttacgag cgttatccac agccgtaaca cgcgcgcgcg attttttaac    10740
tttataaatc tttaacgcgg ttgcggacaa agcccgcgcc gcctcttggg ggctacgccc    10800
ccgccggctc ctacgggccg caagcggccc tccgcccgcg cttcgcgctc cctcccggca    10860
tccccgaggg gtttcgcttc gctgcacccc tcgcgcttcg cgctcacccg catatcgagg    10920
cccccaaagg gggccggatg gtgccccc                                       10948
```

BACTERIAL SECRETOME FOR USE IN THE TREATMENT OF SKIN LESIONS

FIELD OF THE INVENTION

The present invention relates to a novel use of a bacterial secretome in the field of the treatment of skin lesions and more particularly of wound healing. The invention also relates to cosmetic or dermatological compositions comprising such a bacterial secretome as active agent.

PRIOR ART

Wound healing is a complex and dynamic biological process that involves the interaction of many local and systemic factors in normal tissue repair. Healing progresses in three interdependent phases: haemostasis and inflammation, proliferation and remodelling (General principles of wound healing. Witte M B, Barbul A. Surg Clin North Am. 1997 June; 77(3):509-28.). Proliferation involves three clearly observable processes: granulation, contraction and re-epithelialization.

During granulation, cells involved in the repair process are observed to proliferate and migrate toward the wound bed. For example, macrophages, fibroblasts and endothelial cells are found there. Macrophages steadily release chemotactic factors and growth factors. Fibroblasts construct the new cellular matrix necessary to cell growth at the base of the wound. This scaffolding supports cell migration. Lastly, endothelial cells trigger the formation of vascular buds which will establish new capillaries, thereby restoring perfusion and ensuring the supply of oxygen and of nutrients essential to the metabolic activity of cells in the wound.

Wound contraction is a mechanism of reducing wound size, and fibroblasts play a leading role in this contraction.

Re-epithelialization consists in the regeneration of an epidermis that covers a wound to form an effective barrier against the external environment, capable of becoming pigmented and of recovering its sensory and immune functions. It thus involves the cellular processes of keratinocyte migration and proliferation, but also the differentiation of this neo-epithelium and the restoration of a basal membrane connecting the dermis and the epidermis. When the migration of basal cells towards the centre of the wound enables the two wound edges to meet, a wave of cell mitosis occurs to fill the spaces left by the migration and to provide cells for the epithelial tissue in three-dimensional regeneration.

The proliferation stages of keratinocyte cells, fibroblasts and endothelial cells can be regarded as one of the functional phenomena showing the healing activity of an active agent. Increased fibroblast proliferation would participate in the healing of a deep wound (reaching the dermis), whereas increased keratinocyte proliferation would participate in re-epithelialization.

Healing also poses cosmetic problems when healing defects, or poor healing, cause unsightly and mostly permanent visible marks such as thick scars or keloids.

All cosmetic and dermatological surgical procedures, as well as pathological and nonmedical traumatic lesions (scratches, cuts, scrapes, burns), leave scars. One of the principal skills of plastic surgeons is to control scar formation.

Pressure, for example, has been used for many years for burn scars and recently has been combined with silicone sheeting laid directly on the scar.

There remains a need to propose novel compositions for promoting the healing of damaged skin and for improving the cosmetic appearance of scars.

For the first time, and surprisingly, the applicant has shown the beneficial properties in tissue regeneration and in healing of skin lesions of a bacterial secretome derived from a bacterial strain (or bacterium), LMB64, isolated from groundwater.

This bacterium was described by the Applicant in patent application WO2012/085182. More particularly, the bacterium was described as such for its anti-inflammatory activities. Even more particularly, extracts named S0, E0 and ES0 were described and exemplified, said extracts consisting of the culture supernatant separated from the biomass, the biomass of lysed cells, and the supernatant after incubation of the culture at basic pH for several hours, respectively. Only the pharmacological activities of extracts E0 and ES0 were tested, and it was shown that these extracts E0 and ES0 were able to induce cytokines and the maturation of Langerhans cells (for E0) as well as activation of TLR2/TLR4/TLR5, antagonists of PARs, and induction of antimicrobial peptides (for ES0). These results suggested the use of such extracts in the treatment of inflammatory diseases such as pruritis, psoriasis, eczema or atopic dermatitis.

Against all expectations, the Applicant shows herein that a secretome consisting not of the same components as the above-mentioned extracts ES0 and E0, but mainly consisting of the biomolecules secreted and externalized into the culture supernatant by said bacterium LMB64, has surprising healing properties.

DETAILED DESCRIPTION

According to a first embodiment (1), the present invention relates to a bacterial secretome of a non-pathogenic Gram-negative bacterium belonging to the class Betaproteobacteria, subfamily Neisseriaceae, containing a 16S rRNA comprising sequence SEQ ID No. 1, or any sequence having at least 80% identity with sequence SEQ ID No. 1, for use in the treatment of skin lesions, said secretome being likely to be obtained, or obtained, by a process comprising the steps of:
a) culturing said bacterium in a culture medium and under conditions suitable for its growth,
b) liquid/solid separation and recovery of the liquid phase,
c) obtaining said secretome comprising the biomolecules secreted by said bacterium in the liquid phase.

According to a second embodiment of the present invention, the bacterial secretome for use in the treatment of skin lesions according to the invention is characterized in that a basic buffer is added to the liquid phase obtained in step b) and that the buffered liquid phase obtained is optionally left in contact for 1 to 7 h, preferably at a temperature between 1 and 6° C.

Bacterium LMB64 has been characterized and defined as belonging to the class Betaproteobacteria, subfamily Neisseriaceae, and probably a novel genus not yet defined. Analysis of the gene sequence encoding 16S ribosomal RNA (rRNA) made it possible to place this bacterium close to the genera *Chromobacterium, Paludimonas, Lutelia* and *Glubenkiana*, with which it shares 95% sequence similarity.

This non-pathogenic bacterium is Gram-negative and was isolated from groundwater.

More particularly, bacterium LMB64 is rod-shaped with a length of roughly 2.3 µm (±0.3) and a width of roughly 1.0

µm (±0.1). A characteristic feature of this bacterium is the presence of a polar flagellum.

The gene encoding 16S rRNA has been almost completely sequenced (1487 bp, corresponding to sequence SEQ ID No. 1). Bacterium LMB64 has a circular plasmid of 10948 bp. This plasmid was completely sequenced, and the sequence is represented in sequence SEQ ID No. 2.

According to another embodiment, a bacterium from which the secretome of the invention is derived contains at least one plasmid comprising sequence SEQ ID No. 2, or any sequence having at least 80% identity with sequence SEQ ID No. 2, advantageously at least 85%, at least 90%, at least 95%, even at least 97% and more preferentially still at least 98% identity with sequence SEQ ID No. 2.

In addition, a bacterium from which the secretome is derived is a non-pathogenic Gram-negative bacterium belonging to the class Betaproteobacteria, subfamily Neisseriaceae, said bacterium containing a 16S rRNA comprising sequence SEQ ID No. 1, or any sequence having at least 80%, even at least 90%, at least 95%, at least 97% identity with sequence SEQ ID No. 1 and said bacterium containing at least one plasmid comprising sequence SEQ ID No. 2, or any sequence having at least 80% identity with sequence SEQ ID No. 2, advantageously at least 85%, at least 90%, at least 95%, even at least 97% and more preferentially still at least 98% identity with sequence SEQ ID No. 2.

By way of example, such a bacterium is represented by strain LMB64, which was deposited in the name of the Applicant in the Collection Nationale de Cultures de Microorganismes (CNCM), Institut Pasteur, Paris, on 8 Apr. 2010 under number I-4290.

Having this genotypic information, combined with the characteristics concerning growth in sulphur-free medium and the non-filamentous nature of this bacterium, a person skilled in the art would have no difficulty in finding/identifying another bacterium allowing a secretome of the invention to be obtained. Such an identification of another bacterium, of course slightly genotypically different but possessing all the phenotypic criteria of the invention in terms of the secretome, can be made after a selection study, which is in no case insurmountable, and this based on the information contained in the present application and that contained in application WO2012/085182, combined with the general knowledge of the person skilled in the art.

In the context of the present invention, "percentage identity" between two nucleic acid sequences refers to a percentage of identical nucleotides between two sequences to be compared, obtained after the best alignment (optimal alignment), this percentage being purely statistical and the differences between the two sequences being distributed randomly and over their entire length. Comparisons of sequences between two nucleic acid sequences are usually made by comparing these sequences after having aligned them in an optimal manner, wherein said comparison may be made per segment or per "comparison window". The optimal alignment of the sequences for the comparison can be performed, in addition to manually, by means of the local homology algorithm of Smith and Waterman (1981) [Ad. App. Math. 2:482], by means of the local homology algorithm of Needleman and Wunsch (1970) [J. Mol. Biol. 48:443], by means of the similarity search method of Pearson and Lipman (1988) [Proc. Natl. Acad. Sci. USA 85:2444], or by means of computer software using these algorithms (GAP, BESTFIT, FASTA and TFASTA in the Wisconsin Genetics Software Package, Genetics Computer Group, 575 Science Dr., Madison, Wis., or the BLAST N or BLAST P comparison software).

The percentage identity between two nucleic acid sequences is determined by comparing these two aligned sequences in an optimal manner, wherein the nucleic acid sequence to be compared may include additions or deletions in relation to the reference sequence for an optimal alignment between these two sequences. Percentage identity is calculated by determining the number of positions for which the nucleotide is identical between the two sequences, dividing this number of identical positions by the total number of positions in the comparison window, and multiplying the result obtained by 100 to obtain the percentage identity between these two sequences.

For example, the BLAST program "BLAST 2 sequences" (Tatusova et al., "Blast 2 sequences—a new tool for comparing protein and nucleotide sequences," FEMS Microbiol Lett. 174:247-250), available at http://www.ncbi.nlm.nih.gov/gorf/b12.html, may be used with the default parameters (in particular for the parameters "open gap penalty": 5, and "extension gap penalty": 2; with the selected matrix being for example the "BLOSUM 62" matrix proposed by the program). The percentage identity between the two sequences to be compared is calculated directly by the program. It is also possible to use other programs such as the "ALIGN" or "Megalign" software (DNASTAR).

A bacterium of the invention includes bacterium LMB64 which contains at least one plasmid comprising sequence SEQ ID No. 2, or any sequence having at least 80%, preferably 85%, 90%, 95% and 98% identity with said sequence SEQ ID No. 2. Other features of said bacterium LMB64 will be detailed below in the examples.

Moreover, bacterium LMB64 was deposited in the name of the Applicant in the Collection Nationale de Cultures de Microorganismes (CNCM), Institut Pasteur, Paris, on 8 Apr. 2010 under number I-4290.

According to another embodiment, the present invention also relates to a bacterial secretome for use in the treatment of skin lesions according to the second embodiment, characterized in that the basic buffer is selected from Tris buffer, arginine buffer and mixtures thereof.

In another embodiment, the invention relates to a bacterial secretome for use in the treatment of skin lesions according to one of the preceding embodiments, characterized in that step b) of liquid/solid separation is followed by a step b') of clarification of the liquid phase or of the buffered liquid phase by filtration before step c).

In another embodiment, the invention relates to a bacterial secretome for use in the treatment of skin lesions according to the preceding embodiment, characterized in that filtration is carried out with a 0.2 µm cut-off.

According to another embodiment, the invention also relates to a bacterial secretome for use in the treatment of skin lesions according to one of the preceding embodiments, characterized in that said biomolecules consist of the peptides, proteins and secondary metabolites secreted by said bacterium.

It is also another embodiment of the present invention to provide a bacterial secretome for use in the treatment of skin lesions according to one of the preceding embodiments, characterized in that the bacterium contains at least one plasmid comprising sequence SEQ ID No. 2, or any sequence having at least 80% identity with sequence SEQ ID No. 2.

According to another embodiment, the invention also relates to a bacterial secretome for use in the treatment of skin lesions according to one of the preceding embodiments, characterized in that the bacterium is the bacterium deposited with the CNCM on 8 Apr. 2010 under number I-4920.

Generally, the term "secretome" is used to describe all the biomolecules secreted and excreted into the culture medium and solubilized in this medium, by a cell, a tissue or an organism. In the present case, secretome must be understood to refer to all the biomolecules secreted and externalized by bacterium LMB64, and this with no modification, deterioration or lysis of the bacterial cell. More particularly, these biomolecules consist mainly of the proteins, peptides and secondary metabolites secreted and externalized by the bacterium into the culture medium.

Bacteria multiply by binary fission, i.e., each bacterium grows and then divides into two daughter cells separated by a division septum formed by the cell wall. During division, DNA and other components are duplicated. Various enzymatic systems of synthesis and degradation take part in cell division.

Bacterial growth is the ordered increase of all the components of the bacterium. It results in an increase in the number of bacteria. During growth, there is, on the one hand, a depletion of nutrients from the culture medium and, on the other hand, an enrichment in biomolecules secreted and excreted into the culture medium by the bacterium and solubilized in this medium, as well as metabolic by-products.

The expression "culture medium" or "medium" must be understood to refer to any medium comprising at least the nutrients necessary for bacterial growth and multiplication. The bacteria may be grown in liquid, solid or semi-liquid medium. Preferably, the culture medium is a liquid medium allowing recovery of the culture supernatant containing the secretome.

A suitable culture medium contains nutrients which promote bacterial growth and multiplication. Generally, a suitable culture medium will comprise water, a carbon source, a nitrogen source, and salts. By way of illustration, a particular exemplary culture medium is described below in the examples.

The expression "secondary metabolites" must be understood to refer to the small molecules that a bacterium of the invention, in particular bacterium LMB64, produces, secretes and excretes into the culture medium. By way of illustration, such secondary metabolites may be soluble molecules such as bacteriocins, non-ribosomal peptides, siderophores, lipopeptides or polyketides, or molecules such as terpenes, pyrazines, indoles, or sulphide derivatives. The proteins present in the secretome have sizes between 10 kDa and 100 kDa, preferentially between 18 kDa and 98 kDa, and preferably a majority protein whose size is roughly 38 kDa.

In practice, the secretome of a bacterium of the invention, for example and in particular bacterium LMB64, can be obtained from a culture in a culture medium allowing the growth, development and multiplication of the bacterium (as for example that described below) by simply recovering the culture supernatant containing the secreted biomolecules making up the secretome of the invention. In concrete terms, owing to the fact that these biomolecules are secreted and externalized by the bacterium and solubilized in the medium, it is not necessary to perform a step of treating said bacteria (mechanical or chemical, inducing total or partial cell lysis or release of proteins or components of the wall, the membrane or the periplasmic space). The components of the culture supernatant (hereafter the secretome) can be recovered from the insoluble solid cellular components by any liquid/solid separation means. More particularly, it is therefore possible, by the techniques known to persons skilled in the art, to isolate the liquid fraction containing the solubilized biomolecules from the solid fraction containing mostly whole cells and cell debris comprising surface proteins and/or proteins located in the periplasmic space of the bacterium.

By way of illustration, liquid/solid separation can be performed by a technique selected from: centrifugation, sedimentation, filtration, ultrafiltration, decantation, draining, for example.

Preferably, liquid/solid separation is performed by centrifugation of the bacterial culture in order to separate the solid phase, i.e., the pellet, containing cells and cell debris; and the liquid phase, i.e., the supernatant, comprising the soluble molecules, i.e., the secretome.

The supernatant, i.e., the liquid phase, can be used as such, or after simple filtration in order to remove the cell debris possibly present and to sterilize it. It may also be envisaged to concentrate it, for example by diafiltration. The proteins making up the secretome can also be recovered by precipitation with ammonium sulphate.

As indicated above, the process for preparing a bacterial secretome of the invention is characterized in that a basic buffer is added to the liquid phase obtained in step b) and that the buffered liquid phase obtained is optionally left in contact with such a buffer for 1 to 7 h, in particular at low temperature, preferably at a temperature between 1 and 6° C.

The addition of a basic buffer to the supernatant improves the solubility and/or stability of proteins and peptides in solution.

Preferably, this basic buffer is a Tris buffer or an arginine buffer or a Tris-arginine mixture. Preferably it is a Tris-arginine buffer.

The amount of basic buffer, preferentially Tris-arginine, added to the liquid phase is such that the buffered liquid phase obtained has an arginine concentration between 100 mM and 500 mM and/or a Tris concentration between 10 mM and 90 mM.

The pH of the buffered liquid phase may be between 8 and 12, and preferably between 9 and 11.

The use of a basic buffer (Tris, arginine or Tris-arginine) allows stabilization of the proteins in solution and avoids their aggregation over a long storage period.

A preferred method for culturing the bacterium of the invention, in particular strain LMB64, can comprise three steps.

- A first inoculum can be prepared in an Erlenmeyer flask in a suitable medium containing mineral, protein and carbohydrate substances appropriate to this pre-culture.
- A second pre-fermentation culture in batch mode in a second medium similar or identical to the first medium (or any equivalent medium) is then prepared.
- Lastly, fermentation in fed-batch mode in a medium identical or similar to the second medium in order to obtain a high cell density.

A centrifugation step then allows removal of the cells and cell debris and recovery of the culture supernatant.

This buffered supernatant, or buffered liquid phase, can then be clarified by filtration.

As indicated above, step b) of liquid/solid separation is followed by a step b') of clarification of the liquid phase or of the buffered liquid phase, for example by filtration, before step c).

Filtration may be performed by any suitable means allowing clarification of the liquid phase or, if applicable, of the buffered liquid phase. Such clarification by filtration removes the suspended particles not removed during the liquid/solid separation step, and is directed at producing a clear secretome.

Filtration can be performed by any filtration, ultrafiltration or diafiltration means.

Advantageously, filtration is performed by filtration through a filter or a cartridge filter having a 0.4 µm cut-off, preferentially 0.2 µm. In this case, the bacterial secretome is characterized in that the secreted peptides, proteins and secondary metabolites have a size of 0.2 µm or less.

Preferably, non-electrostatically-charged filters or prefilters can be used in order to avoid any absorption of the biomolecules responsible for all or part of the activity.

The exact nature of the media and of the various steps will be described in greater detail in the examples. It must be understood that any modification of the process, of the media, or of the sequences of steps which would be obvious to a person skilled in the art with regard to the present description must be regarded as within the scope of the present patent application.

As mentioned above, the invention also concerns, in another embodiment, a bacterial secretome for use in the treatment of skin lesions according to one of the preceding embodiments, characterized in that the skin lesions are selected from the group consisting of abrasions, burns, sunburns, scratches, cuts, scrapes, stitches.

The invention also relates to a bacterial secretome for use in the treatment of skin lesions according to one of the preceding embodiments for use for the mitigation of healing defects.

The invention also concerns, in another embodiment, a bacterial secretome for use in the treatment of skin lesions according to one of the preceding embodiments, characterized in that the skin lesions follow trauma, surgery, a dermatological procedure, or a cosmetic medicine procedure.

Advantageously, the invention also relates to a bacterial secretome for use in the treatment of skin lesions according to one of the preceding embodiments, characterized in that it is combined with a copper salt or a zinc salt.

In another embodiment, the invention also relates to a bacterial secretome for use in the treatment of skin lesions according to one of the preceding embodiments, characterized in that the treatment of skin lesions consists in improving healing and skin repair.

The invention further concerns, in another embodiment, a method of cosmetic treatment for mitigating skin-healing defects comprising the application of an effective amount of a composition containing an effective amount of a bacterial secretome as defined in one of the preceding embodiments in combination with a cosmetically acceptable excipient and formulated in a form suitable for topical application.

Advantageously, the invention also relates to a bacterial secretome for use in the treatment of healing defects according to one of the preceding embodiments, characterized in that it is combined with a copper salt and/or a zinc salt.

Therefore, the invention further concerns, in another embodiment, the use of a bacterial secretome as defined in one of the preceding embodiments for the mitigating cosmetic treatment of skin-healing defects. According to a particular embodiment, the secretome of the invention is used in combination with a copper salt and/or a zinc salt.

In another embodiment, the invention relates to a dermatological composition containing a bacterial secretome as defined in one of the previous embodiments and a dermatological excipient suitable for topical application. In an advantageous embodiment, the dermatological composition further includes a zinc salt and/or a copper salt.

In another embodiment, the invention further relates to a dermatological composition according to one of the preceding embodiments for use in the treatment of skin lesions. In an advantageous embodiment, the dermatological composition further includes a zinc salt and/or a copper salt.

In another embodiment, the invention relates to a cosmetic composition containing a bacterial secretome as defined in one of the preceding embodiments and a cosmetic excipient suitable for topical application. The cosmetic composition can further include a zinc salt and/or a copper salt.

Lastly, in another embodiment, the present invention relates to the use of a cosmetic composition according to a preceding embodiment for the mitigating cosmetic treatment of skin-healing defects.

According to an embodiment, the invention relates to a bacterial secretome as defined in one of the preceding embodiments, for topical use for promoting fibroblast proliferation.

According to an embodiment, the invention relates to a bacterial secretome as defined in one of the preceding embodiments, for topical use for promoting keratinocyte proliferation and/or migration.

According to an embodiment, the invention relates to a bacterial secretome as defined in one of the preceding embodiments, for topical use for treating skin lesions According to an embodiment, the invention relates to a bacterial secretome as defined in one of the preceding embodiments, for topical use for improving skin healing and recovery.

The invention also relates to a composition for accelerating skin repair in order to restore skin integrity and quality, comprising as active principle the secretome defined in one of the preceding embodiments. More advantageously, the composition can further include a copper salt and/or a zinc salt.

Preferably, the concentration of the secretome in a composition of the invention is between 0.05% and 10%. More preferably, it is between 0.1% and 5%.

The composition of the invention further includes one or more conventional dermatologically and/or cosmetically compatible excipients known to persons skilled in the art in order to obtain a composition for topical application, such as emulsifiers, thickeners, gelling agents, water binders, spreading agents, stabilizers, dyes, fragrances and preservatives.

In the present invention, the expression "dermatologically or cosmetically acceptable" is intended to mean that which is useful in the preparation of a dermatological or cosmetic composition, which is generally safe, nontoxic and neither biologically nor otherwise undesirable and which is acceptable for dermatological or cosmetic use, and in particular dermatological or dermo-cosmetic use, in particular by topical application.

The compositions according to the invention are advantageously for topical application, in particular to the skin.

The composition of the invention can be prepared in the form of an emulsion, a dispersion, or an aqueous or oily lotion.

In another particular embodiment, the dermatological or cosmetic composition of the invention includes at least one other active principle, more particularly at least one moisturizing active principle.

This other active principle may thus particularly be selected from the group consisting of:
  Well-known healing or restorative agents: panthenol, madecassoside, allantoin, aloe vera, honey;
  Anti-infective agents: copper-zinc-type trace elements, honey Moisturizing and nourishing agents: glycerine, shea butter, natural waxes, hyaluronic acid, fatty acids Soothing agents: allantoin, bisabolol, panthenol, enoxolone UV filters.

Preferably, the second active principle will be a copper-zinc-type trace element. In this preferred embodiment, the composition of the invention will thus include the secretome and the copper-zinc-type trace element.

As mentioned, a dermatological or cosmetic composition of the invention comprising the secretome may include a copper salt or a zinc salt. Preferably, the copper salt will be copper sulphate. Advantageously, the zinc salt will be selected from zinc oxide and zinc sulphate.

The amount of copper sulphate in a composition of the invention may vary between 0.05 and 0.5 wt % of the composition, preferentially between 0.1 and 0.25 wt % of the composition, more preferentially roughly 0.2 wt % of the composition.

The amount of zinc sulphate in a composition of the invention may vary between 0.05 and 0.5 wt % of the composition, preferentially between 0.1 and 0.4 wt % of the composition, more particularly between 0.1 and 0.2 wt % of the composition.

The amount of zinc oxide in a composition of the invention may vary between 0.5 and 10 wt % of the composition, preferentially between 1 and 5 wt % of the composition, more particularly roughly 2 to 4 wt % of the composition.

An embodiment of the invention envisages a composition according to one of the preceding embodiments characterized in that it further includes at least one other active principle selected from healing agents, anti-infectives, moisturizing agents, soothing agents and mixtures thereof. According to another particular embodiment, at least one other active principle will be selected from moisturizing agents, healing agents, soothing agents and mixtures thereof, preferably moisturizing agents. Such an active principle will be used preferably in dermatological compositions.

The present invention also relates to a method for treating and healing skin lesions comprising the administration, preferably topical, of an effective amount of a composition containing as active principle a secretome of the invention.

The compositions according to the invention are in particular for the care of skin having sustained lesions.

Skin lesions can appear following trauma or medical or surgical procedures, whether invasive or non-invasive, curative or for cosmetic purposes.

Invasive medical or surgical procedures include: surgical procedures (excision, shaving) with or without stitches, cryotherapy, laser ablation, moderate or strong chemical peels, stitches, mesotherapy or curettage, for example.

Post-traumatic skin lesions, for example following mild external damage to the skin, include cuts, scratches, scrapes and superficial burns or sunburn, for example.

Superficial non-invasive medical procedures requiring a healing product that accelerates skin recovery and is suitable for long-term use (until the skin is completely repaired) include mild chemical peels, laser hair removal, and superficial vascular (rosacea) treatments, for example.

The treatment of skin and mucous membrane lesions of the invention may particularly include the treatment of cuts, stitches, abrasions, scrapes, scratches, scars following surgery or a cosmetic dermatology procedure, superficial burns, sunburn.

The present invention further relates to the use of a cosmetic composition of the invention for improving healing and skin repair and in particular for mitigating healing defects.

The invention will be better understood by reading the examples below which illustrate the invention without limiting it scope.

The examples refer to the following figures

Lane 1 (M, molecular weight markers, Sea Blue).

Lanes 2 to 5: (Sec, secretome before addition of arginine buffer)—10 µl, 15 µl, µl and 30 µl loads, respectively.

Lanes 6 to 9: (Sec+Arg, secretome after addition of arginine buffer)—10 µl, 15 µl, 20 µl and 30 µl loads, respectively.

EXAMPLE 1: CULTURE OF BACTERIUM LMB64

By way of non-limiting example, preferred culture media contain ammonium chloride, magnesium sulphate and yeast extract. It should also be noted that, as arises from application WO2012/085182, among others, other similar media may be used and must thus be regarded as forming an integral part of the present description. Any adaptation by persons skilled in the art must also be regarded as part of the invention.

An exemplary culture process is described below. It should be recalled here that this example is for illustrative purposes only and must in no way be regarded as limiting.

Strain LMB64 is grown in three steps, namely a first inoculum, a pre-culture (or pre-fermentation) in batch mode and finally a culture but in fed-batch mode (addition of glucose).

Inoculum:

A tube of WCB LMB64 is used to inoculate an Erlenmeyer flask containing 1000 mL of sterile medium. The Erlenmeyer flask is then placed in the incubator shaker and shaken. When the cell density of the broth is sufficient, the culture is stopped. The cells are then cooled until transfer to the pre-fermenter.

Pre-Culture:

The pre-fermenter is then filled with roughly 16 L of medium and then fully sterilized.

Two satellite flasks are connected to the pre-fermenter after sterilization of the tank and then of the addition blocks:
   a flask containing a sterile 50% glucose solution. This solution (Glucose batch pre-culture) is immediately transferred to the culture medium to attain the initial glucose concentration of 20 g/L.
   The Erlenmeyer flask containing the inoculum described above in the Inoculum step is inoculated in the pre-fermenter.

The pre-culture is launched and then regulated automatically. By way of example, the following parameters may be mentioned: Temperature, Shaking speed, Pressure, Air flow rate, or $PO_2$.

Cell growth is monitored by measurement of the optical density at 620 nm. The pre-culture is stopped by cooling when it reaches a sufficient density.

Culture:

The fermenter is then filled with 127 L of medium adjusted to pH 7.0 and then fully sterilized. Three satellite flasks are used:

- a flask containing a sterile glucose solution. This solution is immediately transferred to the culture medium to attain the initial glucose concentration of 20 g/L.
- a flask of antifoam. This antifoam will be added automatically during the culture to control the level of foam in the tank.
- a flask of fed-batch glucose. This solution will be added during the culture to promote cell growth.

The culture is launched and then regulated automatically. By way of example, the following parameters may also be mentioned: Temperature, pH, Shaking, Pressure, air flow rate, $PO_2$.

After exhaustion of the glucose initially present in the medium (rise in $PO_2$), addition of the fed-batch glucose solution is triggered, thus enabling high-density cell growth. Fermentation is stopped after total consumption of the glucose. At this stage, the fermentation must is automatically cooled. Throughout the culture, cell growth is monitored by measurement of the optical density at 620 nm. The amount of dry biomass (g/L) obtained at the end of the culture is determined using a weight method.

EXAMPLE 2: EXTRACTION OF THE SECRETOME

The example below is given by way of illustration of a preferred embodiment, but must not be regarded as limiting.

The secretome is obtained, generally, after centrifugation of the result of the culture step in order to remove cells, surface proteins and proteins located in the periplasmic space of the bacterium. This centrifugation step is followed by an addition of a Tris-arginine basic buffer to the supernatant. A last step of filtration of the supernatant is also possible. Any adaptation by persons skilled in the art must also be regarded as part of the invention.

Centrifugation:

The transfer line from the fermenter to the centrifuge is sterilized. The fermentation must is then separated by continuous centrifugation on a centrifuge. Centrifugation is performed at 150 L/h (±30 L/h) with a bowl rotation speed of 10900±1000 rpm. The supernatant is collected in a container fitted with a disposable pouch. The weight of the supernatant is measured on the balance platform.

Addition of Arginine:

The Tris arginine extraction buffer is sterilized and then transferred to the disposable pouch containing the culture supernatant. The contact time necessary is between 1 and 7 hours. The target concentration of Tris and arginine after addition to the disposable pouch is roughly 0.3 M L-arginine and 20 mM Tris.

The total volume after addition of the extraction buffer is roughly 240 L.

Filtration:

Two filtration steps are performed on-line, in order to clarify the supernatant and to produce a clear, germ-free secretome. Filtration is controlled by the filtration/distribution system. The disposable depth-filtration cartridge is placed in its filter housing. All of the filtered product is recovered sterilely in a container fitted with a disposable pouch. The pouch of filtered product is weighed on the balance platform and then stored at +5° C. until distribution.

Gel Electrophoresis of Secretome Proteins: See FIG. 1

Figure 1:
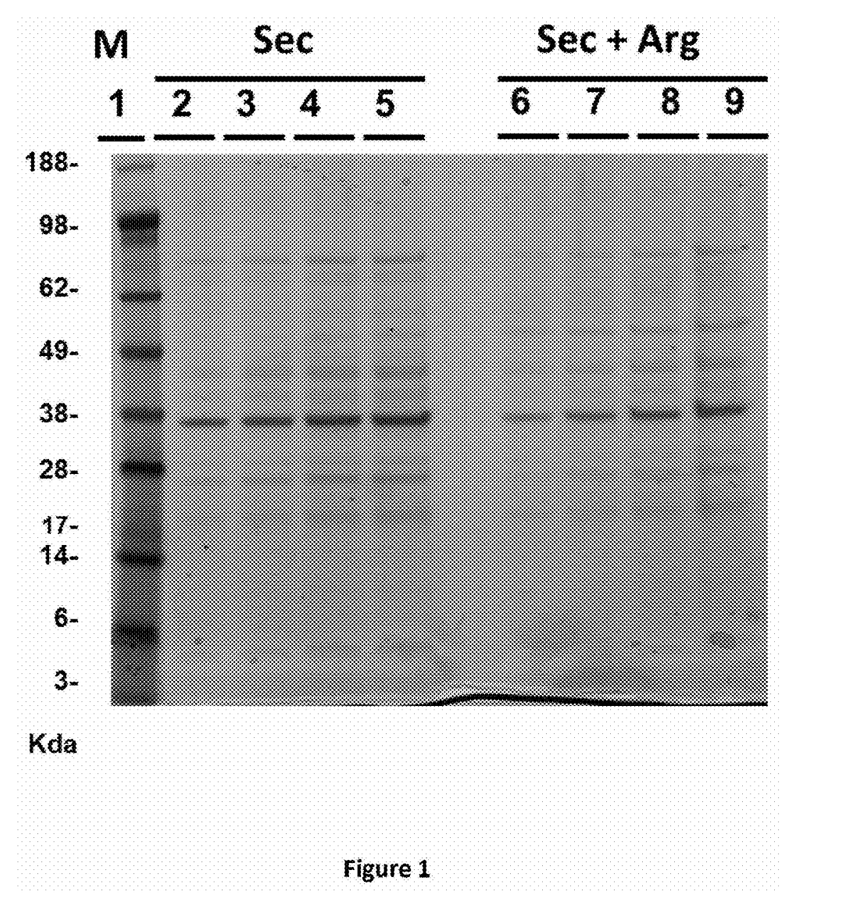
FIG. 1: SDS-PAGE gel of secretome proteins.

Bis-Tris SDS-PAGE gel (4-12%), under denaturing and reducing conditions, detection by Coomassie Blue of the loads of various volumes of culture supernatants (10, 15, 20, 30 µl, respectively) before and after addition of arginine buffer. In both cases, various protein bands of between 14 and 100 kDa in size are observed, including a major band of roughly 38 kDa.

EXAMPLE 3: EFFECT OF THE SECRETOME ON PROLIFERATION OF NORMAL HUMAN FIBROBLASTS

The technique used is that of incorporation of a nucleotide, 5-bromo-2'-deoxyuridine (BrdU), a thymidine analogue, in the DNA of S-phase cells, at 37° C. This technique allows quantification of the cells whose progression in the cell cycle is characteristic of a proliferative cell (S or DNA synthesis phase).

Fibroblasts are seeded in a 96-well plate and then incubated for 72 h in the presence of the compounds to be tested, EGF as positive control and 0.4, 0.6 and 1% secretome. BrdU incorporation is performed during the last 24 h and is quantified using the BrdU ELISA kit (item no. 11647229001, Roche Diagnostics).

The % of the control is calculated according to the formula:

(Value/mean of the control)×100

Stimulation in % is calculated according to the formula:

Mean Stimulation in %=(Mean(Value/mean of the control)×100)−100

SEM=standard dev/√n

Statistical analyses are performed using Student's t-test. The studies were carried out on 3 donor pools.

Figure 2:
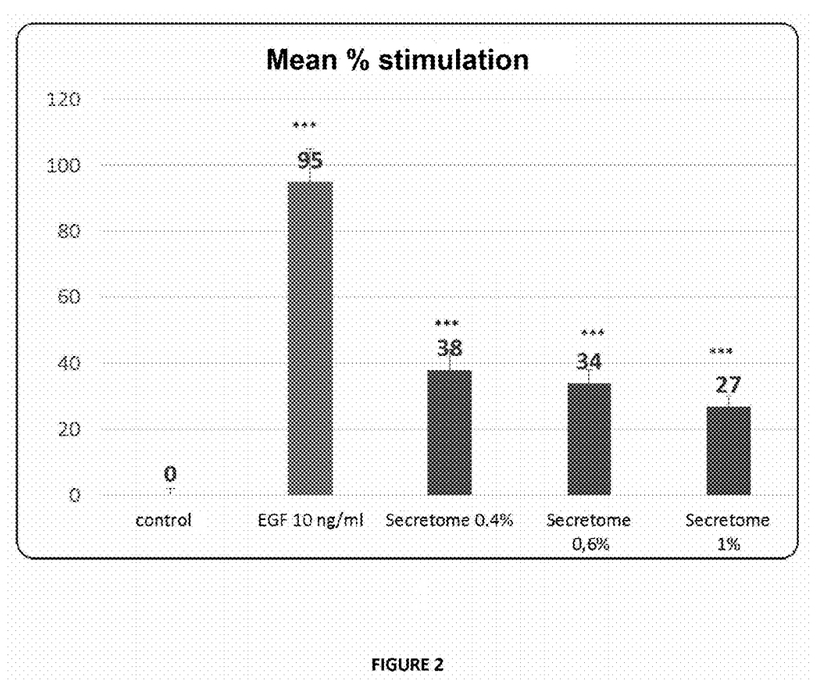
FIG. 2: % stimulation of proliferation (mean±SEM) of normal human fibroblasts treated with the various products compared with control cells (n=3 donor pools).

The positive control, EGF, stimulated fibroblast proliferation strongly and significantly and in a reproducible manner on the 3 donor pools (95% stimulation). This validates the experiments. The results show that the secretome tested at 0.4%, 0.6% and 1% significantly stimulated proliferation of normal human fibroblasts. Table 1 below summarizes the results of BrdU incorporation (mean±SEM) by normal human fibroblasts (by ELISA) after 72 h of incubation in the presence of the tested compounds (n=3 donor pools). The results are shown in FIG. 2.

TABLE 1

| Compound | control | EGF 10 ng/ml | Secretome 0.4% | Secretome 0.6% | Secretome 1% |
|---|---|---|---|---|---|
| Mean % control | 100 | 195 | 138 | 134 | 127 |
| SEM | 2 | 10 | 6 | 4 | 3 |
| Mean % stimulation | 0 | 95 | 38 | 34 | 27 |
| SEM | 2 | 10 | 6 | 4 | 3 |
| Student's t-test | — | *** | *** | *** | *** |

EXAMPLE 4: EFFECT OF THE SECRETOME ON MIGRATION OF THE HACAT KERATINOCYTE CELL LINE

The studies were performed using the Oris Cell Migration Assay (Platypus Technologies) according to the standard protocol recommended by the manufacturer. Chiefly, HaCaT (human keratinocyte cell line) cells are seeded in a 96-well plate. The Oris™ stoppers are removed and the compounds to be evaluated are added to the culture medium. Incubation proceeds for 24 h to allow cell migration. A cell-permeable fluorescent tracer, calcein, is then added to allow visualization of the cells in the zone delimited by the stoppers.

Cell migration is evaluated by photographing the wells and measuring the migration surface area in mm$^2$.

The % of the control is calculated according to the formula:

(Value/mean of the control)×100

Stimulation in % is calculated according to the formula:

Mean Stimulation in %=(Mean(Value/mean of the control)×100)−100

SEM=standard dev/√n

Statistical analyses are performed using Student's t-test.

The studies are performed on 6 technical replicas and in n=2 independent experiments.

Figure 3:
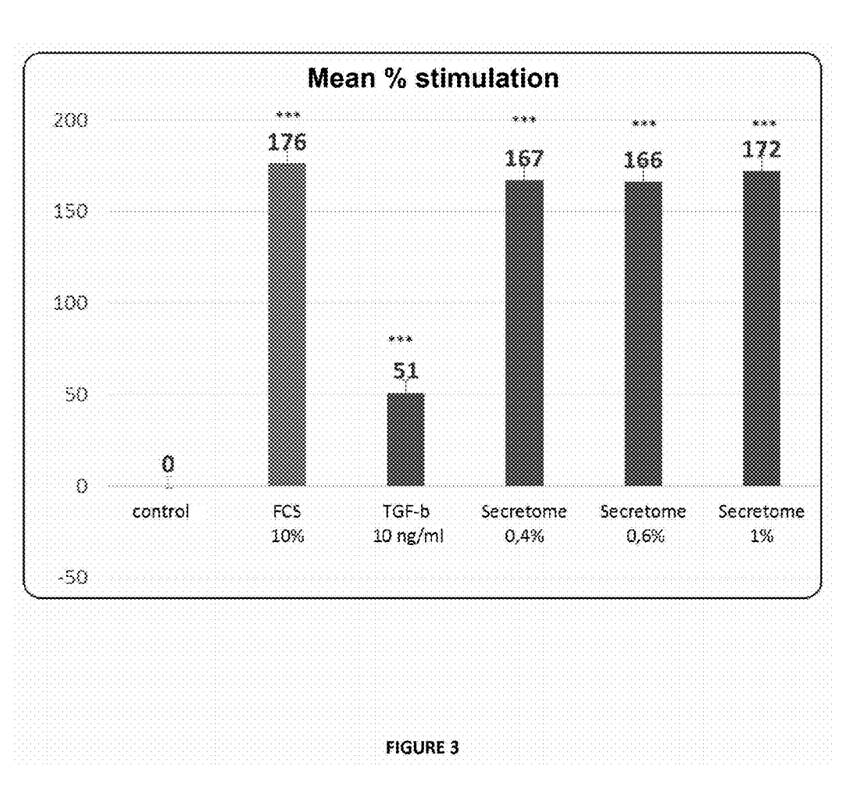
FIG. 3: % stimulation (mean±SEM) of migration of the HaCaT keratinocyte cell line treated with the various compounds compared with control cells (n=2).

The positive controls, TGF-b and foetal calf serum (FCS), stimulated cell migration strongly and significantly and in a reproducible manner (51% and 176% stimulation, respectively). This validates the experiments. The results show that the secretome tested at 0.4%, 0.6% and 1% significantly stimulated HaCaT keratinocyte migration. Table 2 below summarizes the results of HaCaT cell migration after 24 h of incubation with the various compounds (n=2). The results are shown in FIG. 3.

TABLE 2

| compound | control | FCS 10% | TGF-b 10 ng/ml | Secretome 0.4% | Secretome 0.6% | Secretome 1% |
|---|---|---|---|---|---|---|
| Mean % control | 100 | 276 | 151 | 267 | 266 | 272 |
| SEM | 5 | 9 | 7 | 8 | 10 | 9 |
| Mean % stimulation | 0 | 176 | 51 | 167 | 166 | 172 |
| SEM | 5 | 9 | 7 | 8 | 10 | 9 |
| Student's t-test | — | *** | *** | *** | *** | *** |

EXAMPLE 5: EFFECT OF THE SECRETOME ON WOUND CLOSING ON AN EX VIVO MODEL OF HEALING

Skin explants of pig ears are maintained in survival conditions. Six-millimetre biopsies are performed at the centre of which a circular, 3 mm wound is made. The wound damages the entire epidermis and the upper dermis. The products to be evaluated are applied topically. Forty-eight hours later, the biopsies are frozen and haematoxylin-eosin staining is performed on sections. The kinetics of re-epithelialization is evaluated according to the following process:

1) Attribution of a score defined from 0 to 3 according to the protocol developed by J. Brandner (Pollok et al., 2010, J Cell Mol Med).

Precise measurement in m of the extent of the re-epithelialized zone from the wound edge. Student's t-test is applied for significance.

2) The morphological appearance at the wound edge is also evaluated in order to assess tissue preservation quality.

Preparations of the products to be applied: the secretome was added at 0.4, 0.6 and 1 wt % to the same base formulation as that of a reference restorative cream (Cicalfate® cream) tested in parallel. Re-epithelialization is evaluated in comparison with this reference cream.

Figure 4:
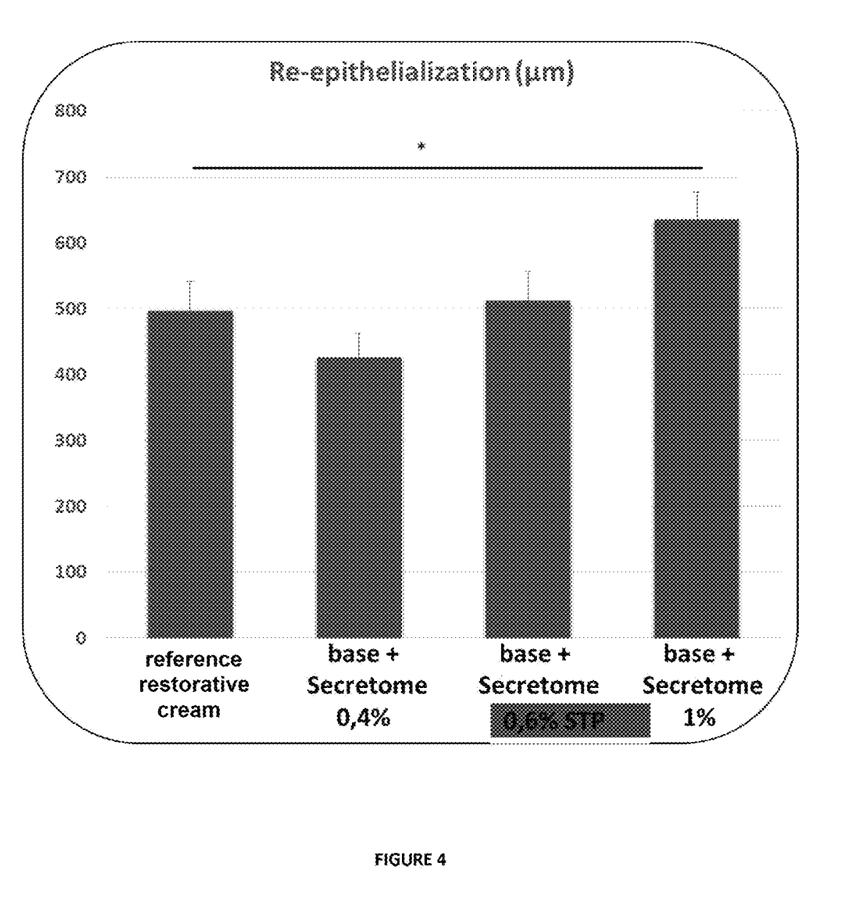
FIG. 4: Wound re-epithelialization (mean±SEM) after application for 48 h on explants of pig ears of the various products compared with a reference restorative cream (n=10 independent donors).

The results show a dose effect with the secretome on the progression of wound re-epithelialization. The formulation containing 1% secretome significantly accelerates the progression of wound closing compared with the reference restorative cream (p=0.043). Furthermore, morphological analysis of the tissues shows an excellent tolerance of the formulations containing the secretome. The results are shown in FIG. 4.

Exemplary Composition: Oil-in-Water Emulsion
Secretome according to Example 2: 0.1-5%
Glycerine: 1-30%
Hexylene glycol: 0.1-7%
Cetearyl glucoside: 0.1-1%
Cetearyl alcohol: 0.9-4%
Stearic acid: 0.5-4%
Glyceryl stearate: 0.1-4%
Vegetable oil: 0.1-10%
Water qs 100%

---

The invention claimed is:

1. A method of treatment of skin lesions which comprises administering to a patient in need thereof a bacterial secretome of a non-pathogenic Gram-negative bacterium belonging to the class Betaproteobacteria, subfamily Neisseriaceae, wherein the bacterium is the bacterium deposited with the CNCM on 8 Apr. 2010 under number 14920, and said secretome is obtained by a process comprising the steps of:
   a) culturing said bacterium in a culture medium and under conditions suitable for its growth,
   b) liquid/solid separation of the culture medium and recovery of the liquid phase,
   c) adding a basic buffer to the liquid phase obtained in step b) and incubating the buffered liquid phase obtained for 1 to 7 hours, optionally at a temperature between 1 and 6° C., and
   d) obtaining said secretome comprising biomolecules secreted by said bacterium in the liquid phase.

2. The method according to claim 1, wherein the basic buffer is selected from Tris buffer, arginine buffer and mixtures thereof.

3. The method according to claim 1, wherein step b) of liquid/solid separation is followed by a step b') of clarification of the liquid phase or of the buffered liquid phase by filtration before step c).

4. The method according to claim 3, wherein the filtration is performed with a 0.2 μm cut-off.

5. The method according to claim 1, wherein said biomolecules comprise peptides, proteins and secondary metabolites secreted by said bacterium.

6. The method according to claim 1, wherein the skin lesions are selected from the group consisting of abrasions, burns, sunburns, scratches, cuts, scrapes, stitches.

7. The method according to claim 1, wherein the skin lesions follow trauma, surgery, a dermatological procedure, or a cosmetic medicine procedure.

8. The method according to claim 1, wherein the treatment of skin lesions comprises improving healing and skin repair.

9. The method according to claim 1, which further comprises administering to the patient a copper salt and/or a zinc salt.

10. The method according to claim 1, wherein the bacterial secretome is contained in a dermatological composition containing the bacterial secretome and a dermatological excipient suitable for topical application, for use in the treatment of skin lesions.

11. The method according to claim 1, wherein the bacterial secretome is contained in a dermatological composition containing the bacterial secretome, a copper salt and/or a zinc salt and a suitable dermatological excipient.

12. A method of treatment of skin lesions which comprises administering to a patient in need thereof a dermatological composition comprising a bacterial secretome of a non-pathogenic Gram-negative bacterium belonging to the class Betaproteobacteria, subfamily Neisseriaceae, a copper salt and/or a zinc salt and a suitable dermatological excipient, wherein
   the bacterium is the bacterium deposited with the CNCM on 8 Apr. 2010 under number 14920, and
   said secretome is obtained by a process comprising the steps of:
   a) culturing said bacterium in a culture medium and under conditions suitable for its growth,
   b) liquid/solid separation of the culture medium and recovery of the liquid phase,
   c) adding a basic buffer to the liquid phase obtained in step b) and incubating the buffered liquid phase obtained for 1 to 7 hours, optionally at a temperature between 1 and 6° C., and
   d) obtaining said secretome comprising biomolecules secreted by said bacterium in the liquid phase.

13. The method according to claim 12, wherein the basic buffer is selected from Tris buffer, arginine buffer and mixtures thereof.

* * * * *